Figure 1:
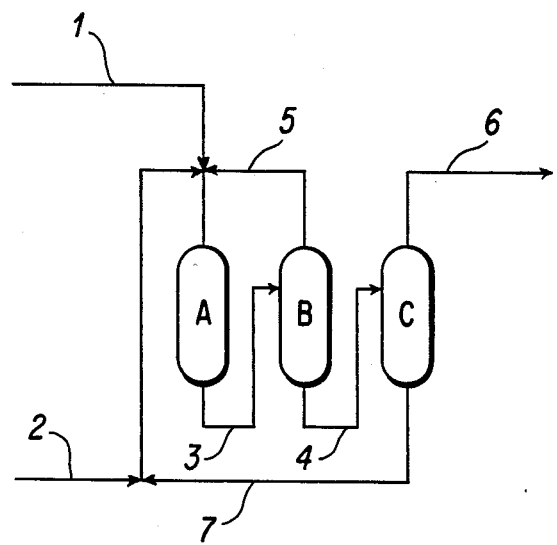

United States Patent [19]

Paparatto

[11] Patent Number: 4,822,929
[45] Date of Patent: Apr. 18, 1989

[54] PROCESS FOR THE CATALYTIC TRANS-HALOGENATION OF A POLYIODO-BENZENE, AND, IN PARTICULAR, OF A DI-IODO-BENZENE

[75] Inventor: Giuseppe Paparatto, Cinisello Balsamo, Italy

[73] Assignee: Montedipe S.p.A., Milan, Italy

[21] Appl. No.: 81,993

[22] Filed: Aug. 5, 1987

[51] Int. Cl.$^4$ ............... C07C 17/15; C07C 17/158
[52] U.S. Cl. .................... 570/203; 570/204; 570/206
[58] Field of Search ............ 570/203, 204, 206, 208, 570/220, 182

[56] References Cited

FOREIGN PATENT DOCUMENTS

| 0183579 | 6/1986 | European Pat. Off. | 570/203 |
| 0077631 | 5/1982 | Japan | 570/204 |
| 2120328 | 6/1987 | Japan | 570/204 |
| 2120329 | 6/1987 | Japan | 570/204 |
| 0368215 | 11/1970 | U.S.S.R. | 570/204 |

*Primary Examiner*—Werren B. Lone
*Attorney, Agent, or Firm*—Stevens, Davis, Miller & Mosher

[57] ABSTRACT

The invention concerns a process for the catalytic trans-halogenation of a poly-iodo-benzene, wherein said poly-iodo-benzene is made to react with benzene and with oxygen, in the presence of a zeolite of the PENTASIL type, exchanged with a metal of the II, III or IV group of the periodical system and anyway present in forms different from the acidic form.

13 Claims, 1 Drawing Sheet

PROCESS FOR THE CATALYTIC TRANS-HALOGENATION OF A POLYIODO-BENZENE, AND, IN PARTICULAR, OF A DI-IODO-BENZENE

BACKGROUND OF THE INVENTION

European patent Nos. 181790 and 183579, in the Applicant's name, disclose a oxy-iodination of benzene, mono-iodo-benzene and small amounts of di-iodo-benzene being thus formed; whilst the mono-iodo derivative can be advantageously used on an industrial scale, e.g., for the manufacture of phenol, the di-iodo-benzenes have not yet found a sufficiently wide application field.

The Applicant has surprisingly found that particular and suitable operative conditions allow the di-iodo-benzenes to be easily trans-halogenated into mono-iodo-benzene, in the presence of oxygen and of benzene, according to the reaction:

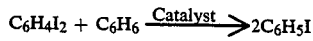

$$C_6H_4I_2 + C_6H_6 \xrightarrow{\text{Catalyst}} 2C_6H_5I$$

DISCLOSURE OF THE INVENTION

In its broadest aspect, the invention concerns a process for the catalytic trans-halogenation of a poly-iodo-benzene and in particular of a di-iodo-benzene, characterized in that said poly-iodo-benzene is reacted with benzene and oxygen—or with other oxygen containing gas,—in the presence of a PENTASIL zeolite, at least partially exchanged with a metal of the II, III or IV group of the periodic system and anyway present in forms different from the acidic form, i.e., from the H form, said zeolite being optionally admixed with an inert binder.

Best results were obtained by using zeolites of the ZSM5 or ZSM11 type, as well as zeolites of the ZSM12 type (mentioned in European patent No. 166,513) and zeolites of the MB28 type (mentioned in European patent No. 21,445, in the Applicant's name), exchanged with alkaline-earth metals and in particular with calcium.

The above process can be very advantageously carried out in parallel to an oxidative iodination of benzene, as disclosed in the above European patents, wherein however, undesired amounts were formed of di-iodo- (and poly-iodo-) benzenes; i.e., at the same time, and inside the same reaction zone, higher yields of mono-iodo-benzene can be obtained (as compared to the simple synthesis from $C_6H_6$ and iodine), because the undesired di-iodo-benzene byproducts can be recycled to the oxy-iodination reaction, thus supplying an additional source of iodine.

According to a preferred form of the invention, the space velocity is from 0.1 to 100 kg/hour of (poly-iodo-benzene+benzene) mixture per Kg of pure zeolite (any binder excluded) and the di-iodo-benzenes (para-, ortho-, or meta-di-iodo-benzene, or their mixtures) are fed to the reaction in the form of a solution in benzene.

One can use either a zeolite in the mono-metal form (e.g., in the calcium form) or a zeolite exchanged with two or more different cations.

Our catalyst can be prepared from the acidic form of the zeolite, by first partially exchanging the proton with the cation of one of the desired metals (using the solution of a water-soluble salt thereof) and subsequently neutralizing all of the residual acidic sites with the diluted solution of the hydroxide of a metal different from the preceding one; by using this latter technique, a completely exchanged catalyst is obtained, and all of the Brönsted's acidic sites, responsible for the decay of the catalytic activity, are eliminated.

The PENTASIL zeolites, exchanged, before being used, with at least a divalent or trivalent cation (preferably selected from $Zn^{++}$ cation and the cations of the alkaline-earth metals) can be used as such, or admixed with a suitable amount of an inert agent, e.g., $SiO_2$, which is acting as a binder and/or carrier. When a thus exchanged zeolite is used, a stabilization is observed; when, on the contrary, the same PENTASIL zeolites are used in their acidic form, or in their alkaline form, a decay is observed in their activity. In the preparation of the exchanged PENTASIL zeolites, one can start either from their sodium form, or from their acidic form. In the first case, the sodium is exchanged with the desired cation, by using known technologies. In the second case, the preparation is carried out starting from the acidic form. Although the exchange technique can be still used, the neutralization technique is more convenient. In such a case, an aqueous solution is used of a salt of the cation which yields, by hydrolysis, a basic pH (or, still better, a diluted aqueous solution is used of the hydroxide of the metal cation). This latter method gives the certainty that a zeolite lacking Brönsted's acidic sites is obtained. The catalytic system can be consisting also of zeolites exchanged with two or more cations. The results of the invention are very surprising; the same PENTASIL zeolites infact, when in their acidic form or exchanged with cations different from the ones of the invention promote a reaction in the opposite direction, i.e., the conversion of mono-iodo-benzene into poli-iodo-benzene.

The trans-iodination can be carried out according to the most different ways, however always within the scope of the invention. According to a very advantageous form, the reaction temperature is from 350° to 450° C.; the benzene/poly-iodo-benzene molar ratio is from 100 to 1 (preferably from 20 to 1); the poly-iodo-benzene:$O_2$ molar ratio is from 10 to 0.05 (preferably from 5 to 0.5) and the reaction is carried out over a fluidized bed or over a fixed bed of catalyst. Further optional operative details are reported hereinafter.

A solution of di-iodo-benzenes in benzene (at a concentration from 0.5 to 50%, preferably from 5 to 20% by weight) is evaporated and admixed with oxygen or air (oxygen is preventing iodine from being formed) and the mixture is fed to a fixed-bed reactor, loaded with the catalyst, an inert diluent, e.g. nitrogen, being optionally used. The products can be recovered by cooling the stream leaving the reactor and resorting to usual treatments. In the case of a distillation, benzene is distilled as the overhead fraction and can be recycled to the reactor. The total pressure is usually not much higher than atmospheric pressure; lower or higher pressures can be however used. The activity decreases under the admissible level, a regeneration is started; said regeneration can be consisting of a heat treatment in air, for some hours, at 300°–550° C.

According to an alternative and very efficacious regeneration a benzene stream, optionally admixed with air or other oxygen-containing gas, is made to flow over the exhausted catalyst at 300°–550° C.

Also the initial activation of the catalyst is an important step; in general, an activation in air at 450°–550° C. or the methods disclosed in European patent Nos. 168,978; 169,026; and 169,027 can be used.

Figure 2:
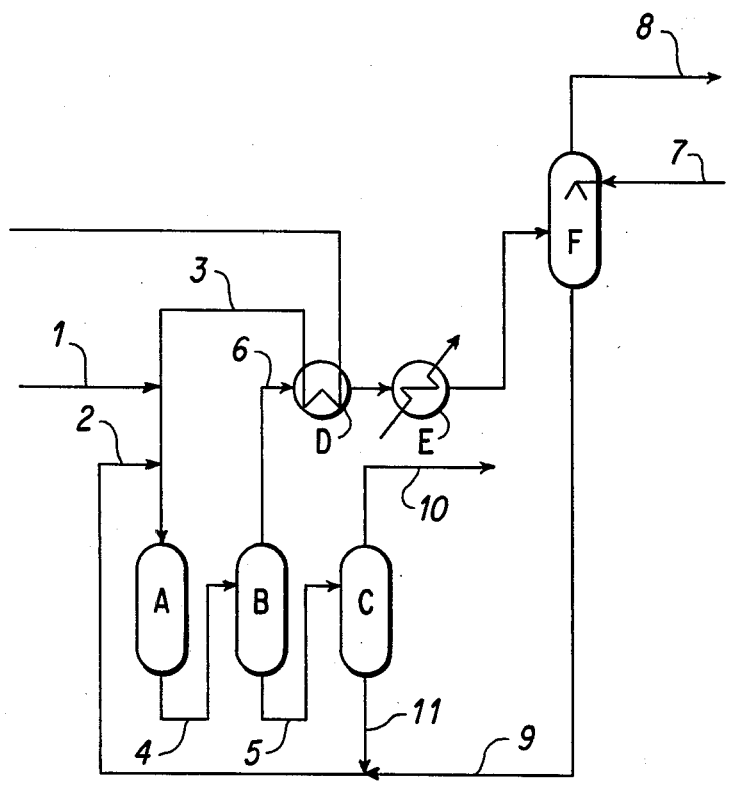

The invention is described also with the aid of some figures, which are however in no way limitative of the scope of the same invention:

FIG. 1 concerns a simple trans-halogenation:

FIG. 2 provides a parallel oxidative and catalytic mono-iodination of benzene with iodine.

Following the flow diagram of FIG. 1, benzene, admixed with oxygen (1) and a solution containing one or more di-iodo-benzenes (2), enter, in the gas phase, reactor (A), loaded with the catalyst; the raw reaction effluent (3) is cooled (inside heat exchangers and heat recovery units, not shown on the Figure) and transferred to separator B, from the bottom of which mono-iodo-benzene and residual di-iodo-benzenes are withdrawn (4), while the most part of the unreacted benzene and oxygen (5) are recycled to the trans-halogenation reaction. Distillation tower C allows the fractionation of the halogenated compounds; iodo-benzene (6) leaves the tower as the overhead fraction and the residual di-iodo-benzenes (7), admixed with a portion of mono-iodo-benzene and with a small amount of benzene, are recycled to the reaction zone.

According to FIG. 2, a solution, containing iodine in an excess of benzene (1), and a solution containing one or more di-iodo-benzenes (2) enter, in the gas phase, reactor A, together with a pre-heated stream of air (or of other oxidating gas) (3); the raw effluent from the simultaneous reactions of iodination and trans-iodination (4) is cooled (inside facilities not shown on the Figure) and transferred to separator B, from the bottom of which one withdraws a solution containing iodo-benzene and residual di-iodo-benzene, together with a small amount of benzene (5); whilst the most part of the unreacted benzene, admixed with nitrogen-enriched air (6), is cooled in the recovery unit D and in cooler E before entering the separation and benzene recovery tower F (two towers in series are preferable), where the scrubbing liquid (7) can be consisting of benzene, iodo-benzene, di-iodo-benzenes or their mixtures. The nitrogen-enriched air (8) can be vented (or transferred to other units) and the excess benzene (9) is recycled. Distillation tower C allows the fractionation of the halogenated compounds; iodo-benzene (10) outflows as the overhead fraction, and the residual di-iodo-benzenes (11) leave the tower bottom as the tail products and are combined with recycle stream (9). All the iodine feed is thus completely used, the iodine dispersed in the undesrred byproducts (poly-iodo-benzenes) being completely recovered (by means of trans-halogenation). The following Examples are illustrating the invention, without however being in any way limitative of the scope thereof.

EXAMPLE 1 (Comparative; H-ZSM5)

A ZSM5 zeolite was prepared in a raw form, according to Example No. 24 of U.S. Pat. No. 3,702,886, and subsequently exchanged at 80° C. with a 1 M solution of HCl, for obtaining the sodium-free (H-ZSM5) form. The zeolite crystallites had an average size lower than 0.5 micrometers; 1 g of the thus obtained zeolite was admixed with 0.3 g of binder ($SiO_2$) and the whole mixture was activated in air for 2 hours at 540° C.; the resulting catalyst was loaded into a quartz microreactor, kept at 400° C. and continuously fed with a mixture, in the gas phase, of benzene, p-di-iodo-benzene (p-DIB) and air, with a benzene:p-DIB: air molar ratio of 20:1:20. The pressure was slightly higher than 760 mmHg and the weight hourly space velocity (WHSV) was 6 kg/h of (benzene+di-iodo-benzene) mixture per kg of pure zeolite (binder excluded). The reaction continued for 1 hour and the reaction products were collected by condensation; the conversion of p-DIB was very low (10%) and the selectivity to iodo-benzene (based on converted p-DIB) was 99%.

EXAMPLE 2 (Comparative; Na-ZSM5)

Example 1 was repeated using a Na-ZSM5 zeolite, obtained by neutralization of the acidic form H-ZSM5 with diluted aqueous NaOH, followed by washing with de-ionized water and by an activation at 540° C. The conversion of di-iodo-benzene was lower than 5%.

EXAMPLE 3

Example 1 was repeated using a Ca-ZSM5 zeolite obtained by neutralization of the acidic form H-ZSM5 with a saturated solution of $Ca(OH)_2$ (at 80° C. for 2 hours), followed by a washing with deionized water and by activation at 540° C. for 2 hours. After a 6-hour reaction time, the conversion of di-iodo-benzene was 60%, and the selectivity to iodo-benzene was higher than 99%.

What I claim is:

1. A process for the manufacture of mono-iodo-benzene by means of a catalytic trans-halogenation of a poly-iodo-benzene, characterized in in that said poly-iodo-benzene is reacted at 350°–450° C. with benzene and an oxygen-containing gas in the presence of a zeolite of the PENTASIL type, at least partially exchanged with a metal of Group II, III or IV of the Periodic System.

2. A process according to claim 1, wherein the trans-halogenation takes place in parallel to an oxidative mono-iodination of benzene with elemental iodine, minor proportions of poly-iodo-benzenes, in particular di-iodo-benzenes, being consequently formed, said poly-iodo-benzenes being recycled, as an additional iodine source, to the reaction zone, where said trans-halogenation and said mono-iodination reactions take place simultaneously.

3. A process according to claim 2, wherein the benzene:poly-iodo-benzene molar ratio is from 100 to 1.

4. A process according to claim 2, wherein the poly-iodo-benzene:oxygen molar ratio is from 10 to 0.01.

5. A process according to claim 2, wherein the space velocity is from 0.1 to 100 kg/h of poly-iodo-benzene+benzene, mixture per kg of pure zeolite, any binder excluded.

6. A process according to claim 2, wherein the poly-iodo-benzene is fed as a solution in benzene, at a concentration from 0.5 to 50% and preferably from 0.5 to 20% by weight.

7. A process according to claim 2, wherein the zeolytic catalyst is a zeolite of the ZSM5 type, exchanged with an alkaline-earth metal and in particular with calcium.

8. A process as defined in claim 1, wherein the poly-iodobenzene is a di-iodo-benzene.

9. A process for the catalytic manufacture of mono-iodo-benzene by means of a trans-halogenation of a di-iodo-benzene, wherein said di-iodo-benzene is reacted at 350°–450° C. with air or other oxygen-containing gas in the presence of a ZSM-5 zeolite, at least partially exchanged with an alkaline-earth metal, according to benzene:di-iodo-benzene: molar ratios from 1 to 20, and di-iodo-benzene: $O_2$ molar ratios from 5 to 0.5, and at a space velocity from 0.1 to 100 kg/h of di-iodo-benzene+benzene mixture per kg of pure zeolite.

10. A process according to claim 9, wherein the reaction takes place inside a fluidized bed of catalyst.

11. A process according to claim 9, wherein the reaction takes place over a fixed bed of catalyst.

12. A process according to claim 9, wherein the catalyst is regenerated at 300°–550° C., by means of a benzene stream, optionally admixed with air or with other oxygen-containing gas.

13. A process as defined in claim 9, wherein the alkaline-earth metal is calcium.

* * * * *

UNITED STATES PATENT AND TRADEMARK OFFICE
CERTIFICATE OF CORRECTION

PATENT NO. : 4,822,929
DATED : April 18, 1989
INVENTOR(S) : Giuseppe PAPARATTO

It is certified that error appears in the above-identified patent and that said Letters Patent is hereby corrected as shown below:

In the heading of the patent between items [22] and [51], insert:

--(30) Foreign Application Priority Data
August 11, 1986 (IT) 21464 A/86--

Signed and Sealed this

Eighth Day of May, 1990

Attest:

HARRY F. MANBECK, JR.

Attesting Officer     Commissioner of Patents and Trademarks